United States Patent
Bertino et al.

(10) Patent No.: US 8,822,421 B2
(45) Date of Patent: Sep. 2, 2014

(54) E2F AS A TARGET OF HORMONE REFRACTORY PROSTATE CANCER

(75) Inventors: Joseph R. Bertino, Brantford, CT (US); Debabrata Banerjee, Bellerose, NY (US); Tamara Minko, Somerset, NJ (US); Olga B. Garbuzenko, Highland Park, NJ (US); Xiaoqi Xie, Lawrenceville, NJ (US); John E. Kerrigan, East Windsor, NJ (US); Emine E. Abali, Tenafly, NJ (US); Kathleen W. Scotto, Washington Crossing, PA (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/274,118

(22) Filed: Oct. 14, 2011

(65) Prior Publication Data

US 2012/0093919 A1    Apr. 19, 2012

Related U.S. Application Data

(63) Continuation-in-part of application No. PCT/US2010/031098, filed on Apr. 14, 2010.

(60) Provisional application No. 61/212,699, filed on Apr. 14, 2009.

(51) Int. Cl.
*A61K 38/00* (2006.01)
*A61K 31/4436* (2006.01)
*C07K 14/47* (2006.01)
*A61K 38/08* (2006.01)
*A61K 31/519* (2006.01)
*A61K 31/513* (2006.01)
*A61K 45/06* (2006.01)

(52) U.S. Cl.
CPC ......... *C07K 14/4703* (2013.01); *A61K 31/4436* (2013.01); *A61K 38/08* (2013.01); *A61K 31/519* (2013.01); *A61K 31/513* (2013.01); *A61K 45/06* (2013.01)
USPC ....................................................... 514/19.3

(58) Field of Classification Search
None
See application file for complete search history.

(56) References Cited

FOREIGN PATENT DOCUMENTS

WO    0351312 A2    6/2003

OTHER PUBLICATIONS

Arakawa et al, Factors affecting short-term and long-term stabilities of proteins, Advanced Drug Delivery Reviews, 46, 307-326 (2001).
Wang, Instability, stabilization, and formulation of liquid protein pharmaceuticals, International Journal of Pharmaceutics 185, 129-188 (1999).
Crowe, et al., The Trehalose Myth Revisited: Introduction to a Symposium on Stabilization of Cells in the Dry State, Cryobiology 43, 89-105 (2001).

*Primary Examiner* — Thomas Heard
(74) *Attorney, Agent, or Firm* — Fox Rothschild LLP

(57) ABSTRACT

The instant invention provides amino acid sequences competing with E2F for DNA binding. Methods of using said amino acid sequences for treatment of hormone-refractory prostate cancer are also provided.

11 Claims, 8 Drawing Sheets

Experimental Peptide:

NH2-RQIKIWFQNRRMKWKKHHHHRLSH-OH

Drosophila penetratin sequence   heptamer

Control Peptide:

NH2-RQIKIWFQNRRMKWKKAAAVLSA-OH

Drosophila penetratin sequence   Scrambled sequence

Fig. 7
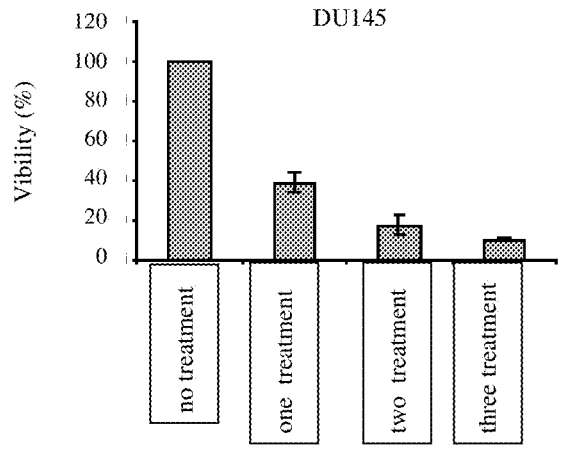
Fig. 8
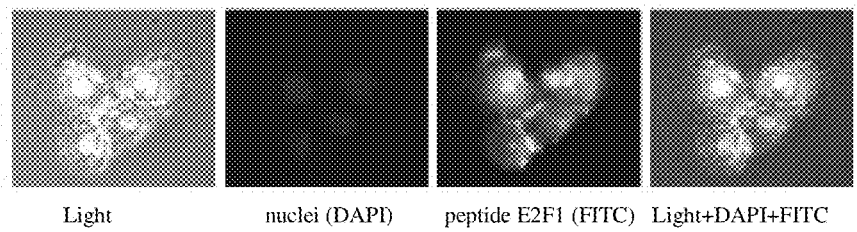
Light     nuclei (DAPI)     peptide E2F1 (FITC)     Light+DAPI+FITC
Fig. 9
Experimental Peptide:
NH2-RQIKIWFQNRRIKWKKHHHRLSH-OH
NH2- ▮▮▮▮▮▮▮▮▮▮▮▮▮▮▮▮▮▮▮▮▮▮▮▮ -OH
      Drosophila penetratin sequence    heptamer

E2F AS A TARGET OF HORMONE REFRACTORY PROSTATE CANCER

RELATIONSHIP TO PRIOR APPLICATIONS

This is a Continuation-in-Part of Patent Cooperation Treaty Patent Application Serial Number PCT/US2010/031098 filed Apr. 14, 2010, which in turn claims priority to U.S. Provisional Patent Application Ser. No. 61/212,699 filed on Apr. 14, 2009, and are incorporated herein by reference.

GOVERNMENTAL SUPPORT

The research disclosed in this application was funded by National Cancer Institute Grant No. CA08010. Accordingly, US Government has certain rights in this invention.

FIELD OF INVENTION

The instant invention is related to inhibitors of E2F activity and their use for treatment of hormone refractory prostate cancer.

BACKGROUND

Prostate cancer is the most common type of cancer found in American men, other than skin cancer. Prostate cancer is the second leading cause of cancer death in men. (Lung cancer is the first.) One man in 6 will get prostate cancer during his lifetime. And one man in 35 will die of this disease. More than 2 million men in the United States who have had prostate cancer at some point are still alive today. In 2009, there were over 190,000 new cases of prostate cancer, and over 27,000 deaths from prostate cancer (American Cancer Society).

Prostate cancer has been treated with hormonal therapy, surgical therapy, radiation therapy, or chemotherapy, or combinations thereof. Hormonal therapy suppresses the production or activity of androgen which is involved in the growth of prostate cancer. The hormonal therapy is carried out by removing testicles that produce androgen, or by administering an LH-RH analog that acts on the pituitary gland and reduces the level of testosterone, an estrogen preparation, or an anti-androgen agent, etc. Hormonal therapy is the only therapeutic method available for treating advanced prostate cancer. However, many advanced prostate cancer patients acquire hormone resistance several years after starting hormonal therapy, and they struggle with the treatment.

Expression of E2F-1, an "activating" E2F transcription factor, is low in benign and localized prostate cancer, modestly elevated in involved lymph nodes and highly elevated in metastatic tissues from patients with hormone refractory prostate cancer. E2F-1, compared to other E2Fs, has a unique role in that it triggers both apoptosis and proliferation via activation of downstream target genes. Target genes activated by E2F include dihydrofolate reductase (DHFR), thymidylate synthase (TS) and thymidine kinase (DeGregori et al, 2006). Recent evidence also shows E2F-1 can activate the miR-106b-25 cluster, via inhibition of TGFβ interference with the expression of p21 and BCL2L11(BIM) (Petrocca et al, 2008). Therefore in cells with dysregulated and high expression of E2F-1, which drives tumor growth, inhibition of E2F1 expression leads to cell death. Furthermore, the downstream target genes, DHFR and TS are decreased by E2F1 inhibition, allowing the potential for synergistic cell kill with an inhibitor of E2F-1 along with inhibitors of these enzymes, (e.g. methotrexate and 5-fluorouracil). Of interest, MTX and 5 FU are less efficacious in prostate cancer treatment as high E2F-1 levels increase resistance to these drugs (Li et al 1995). Decreasing DHFR and TS expression may increase sensitivity to these inhibitors. Accordingly, E2F levels are elevated in hormone refractory prostate cancer and its role in cellular proliferation makes the E2F-1 transcription factor an attractive target for therapy.

Accordingly strategies for inhibiting E2F-1 function using peptides have been suggested. There is precedent for this approach and several groups have devised strategies based on blocking the DNA binding function of the E2Fs. The main approaches reported to inhibit the function of E2Fs are: a) using dominant negative E2Fs or using antisense oligonucleotides to inhibit E2F synthesis, or decoys (Isizaki et al, 1996; Mann et al, 1999; Kaelin 2003), or, b) using decoy dominant inhibitory proteins or peptides that interfere with the E2F-DNA interaction (Bandera et al, 1997; Fabbrizzio et al, 1999; Ma et al, 2008). However none of these strategies have been completely satisfactory and there remains a need for additional treatment strategies.

Thus, there is a need in the art for effective therapeutic methods for treating prostate cancer that has acquired resistance to the hormonal therapy.

SUMMARY OF INVENTION

The instant invention addresses these and other needs in the art, by providing, in one aspect, an amino acid sequence comprising HHHRLSH (SEQ ID NO: 1), which is useful for treatment of prostate cancer. SEQ ID NO: 1, optionally used as a fusion peptide with *Drosophila* derived fragment of Antennopedia protein RQIKIWFQNRRMKWKK (SEQ ID NO: 2) or RQIKIWFQNRRIKWKK (SEQ ID NO: 33) also known as penetratin. In certain embodiments, the resulting protein comprises, consists essentially of, or consists of SEQ ID NO: 3 (RQIKIWFQNRRMKWKKHHHRLSH) or SEQ ID NO: 34 (RQIKIWFQNRRIKWKKHHHRLSH). The inventors have surprisingly discovered that SEQ ID NO: 1 or SEQ ID NO: 3 or SEQ ID NO: 34 are capable of binding a recognition site for E2F-1 factor (TTTNNCGC, wherein N is C or G (SEQ ID NO: 4)) in the promoter of the target gene.

In another aspect, the invention relates to a use of the protein according to any embodiments of the previous aspect of the invention for the manufacture of a medicament for treatment of a cancer. In one embodiment, the cancer is a hormone refractory prostate cancer. In other embodiments, the cancer may be selected from the group consisting of solid or liquid tumors. In different embodiments, the solid tumors are selected from brain cancer, lung cancer, stomach cancer, duodenal cancer, esophagus cancer, breast cancer, colon and rectal cancer, bladder cancer, kidney cancer, pancreatic cancer, prostate cancer, ovarian cancer, mouth cancer, eye cancer, thyroid cancer, urethral cancer, vaginal cancer, neck cancer, lymphoma, and the like. In another embodiment, the lung cancer may be selected from the group consisting of non-small cell lung cancer (NSCLC), small cell lung cancer, bronchioloalveolar carcinoma (BAC), squamous carcinoma and adenocarcinoma of the lung. In other embodiments, different cancers of blood cells are amenable to treatment. These blood cancers include, without limitations, Acute lymphocytic leukemia, Chronic myelogenous leukemia, Chronic lymphocytic leukemia, lymphomas. Hairy cell leukemia, and myeloma. Preferably, although not necessarily, the cancer is characterized by the lack of expression of functional retinoblastoma protein (pRb).

In one embodiment of invention, the protein of the instant invention is administered in conjunction with an inhibitor of dihydrofolate reductase, thymidylate synthase and ribonucleotide reductase, such as, for example, methotrexate or 5-fluorouracil. In different embodiments, the protein and the inhibitor may be administered simultaneously, or the inhibitor may be administered before or after the protein.

The protein and/or the inhibitor may be administered by multiple routes which, in different embodiments, are independently selected from the group consisting of orally, topically, intravenously, intraarterially, intramuscularly, intracolonically, intracranially, intrathecally, intraventricularly, intraurethrally, intravaginally, sub-cutaneously, intraocularly, intranasally, and any combinations thereof.

BRIEF DESCRIPTION OF THE DRAWINGS

FIG. 7 is a chart of viability ratio after repeated incubations with PEP, which indicates that daily addition of PEP increases cell sensitivity to the peptide.

FIG. 8 is an illustration of distribution of the PEP incapsulated in PEGylated liposomes, which demonstrates cytoplasmic and nuclear distribution of the peptide.

FIG. 9 is an illustration of a penetratin-peptide (PEP-2) (SEQ ID NO: 34).

DETAILED DESCRIPTION OF PREFERRED EMBODIMENTS

Figure 1A:
FIG. 1 is an illustration of the effect of the experimental penetratin-peptide (PEP-1) (SEQ ID NO: 3) and a control penetratin-peptide (SEQ ID NO: 19) on growth inhibition in certain tumor cell lines.
Figure 1A:

For the purpose of a better understanding of the invention, the following non-limiting definitions will be provided.

The terms "treat," "treatment" and the like refer to executing a protocol, which may include administering one or more drugs to a patient (human or otherwise), in an effort to alleviate signs or symptoms of the disease. Alleviation can occur prior to signs or symptoms of the disease appearing, as well as after their appearance. In addition, "treating" or "treatment" does not require complete alleviation of signs or symptoms, does not require a cure, and specifically includes protocols which have only a marginal effect on the patient. In this instant, treatment involves use of this invention as a single delivery therapeutic, or multiple or repeated delivery therapeutic, or a control delivery therapeutic and is meant to be delivered locally, systemically, intravascularly, intramuscularly, intraperitoneally, inside the blood-brain barrier, or via other various routes. For example, the term "cancer treatment" may refer on a cellular level to a reduced rate of tumor growth and/or increased apoptosis of tumor cells, compared to untreated cells or cells treated with vehicle. According to this definition, the growth is reduced by at least 10% (e.g., 25%, 50%, 75%, 80%, 85%, 90%, 95%, or 99%) or the apoptosis is increased by at least 10% (e.g., 25%, 50%, 75%, 100%, 150%, 200%, etc).

The term "patient" refers to a biological system to which a treatment can be administered. A biological system can include, for example, an organ, a tissue, or a multi-cellular organism. A patient can refer to a human patient or a non-human patient.

The term "about" refers to a range of values within ten percent (10%) of a baseline value. Thus, for example, the phrase "about 50" refers to a range of values between 45 and 55.

The retinoblastoma protein (pRb) controls E2F transcription factor function; deregulation of the components of this pathway is found in many human cancers. To date, nine members of the E2F family have been identified. Broadly, E2Fs-1-3a are generally considered to be transcriptional activators of genes, while E2Fs 3-6 are repressors of E2F gene function. The E2Fs are involved in mitosis, DNA repair, and differentiation, among other important cellular functions. E2F-1 is unique among the E2F family of transcription factors in that it is both an oncogene, stimulating tumor growth, and also can induce apoptosis when overexpressed. According to the latest research, dysregulation of E2F family members is a hallmark of cancer. However, the roles of the different E2F family members in the process of tumorigenesis are still being elucidated. E2F-1 levels are increased in some human cancers and increased E2F-1 expression correlates with more aggressive tumors and poorer outcome in certain cancers such as non-small cell lung cancer and malignant melanoma. Importantly, E2F-1-3a inhibition results in down regulation of proteins that are targets for clinically useful chemotherapeutic drugs. As a result drugs that target these enzymes together with agents that lower E2F activity would be predicted to result in enhanced anti-tumor effects.

One goal of the instant invention is to find peptides which interfere with the binding of E2F to its recognition sequences on the promoters of respective target genes. To that effect, phage display technique was utilized, as discussed in the examples. The inventors identified four heptamer peptides that bind consensus E2F recognition site. These peptides are His HisHisArgLeuSerHis (SEQ ID NO: 1), HisArgProTrp IleAlaHis (SEQ ID NO: 7), HisAlaIleTyrProArgHis (SEQ ID NO: 8), ProGluTyrAspProTyrPhe (SEQ ID NO: 9). Accordingly, one aspect of the invention relates to amino acid sequences, comprising, respectively, SEQ ID NOs 1, 7, 8, and 9. In another embodiments, the amino acid sequences of the instant invention may consist essentially of those sequences, i.e., the amino acids of the instant invention include the recited sequences but do not include other sequences that affect cell survival or cell death independently of SEQ ID NOs 1, 7, 8, or 9.

In yet another set of embodiments, variants of these amino acid sequences may be used. The variants of the aforementioned sequences comprise heptamer sequences that are 5/7 identical to the recited sequence, i.e., no more than two amino acids are different between the recited sequence and its variant. Further, the differing amino acids must be structurally similar, i.e., the substitution must be conservative.

Conservative substitution tables providing functionally similar amino acids are well known in the art. Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Gly, and Asp/Glu.

The amino acid sequences consisting essentially of SEQ ID NOs 1, 7, 8, 9 or variants thereof or the amino acid sequences comprising SEQ ID NOs 1, 7, 8, 9 or variants thereof may include cell-penetrating amino acid sequences, including without limitations Antennopedia peptide, SEQ ID NO: 2, SEQ ID NO: 33, HIV-TAT, VP-22, a growth factor signal peptide sequence or any combination thereof and other sequences known in the art that enhance peptide uptake. In one embodiment, the cell-penetrating amino acid sequence consists of, or consists essentially of, or comprises SEQ ID NO: 2 or a variant or a derivative thereof. The methionine residue in SEQ ID NO: 2 may be substituted with isoleucine or another amino acid with a hydrophobic side chain. In another embodiment, the cell-penetrating amino acid sequence consists of, or consists essentially of, or comprises SEQ ID NO: 33 or a variant or a derivative thereof. Preferably, these cell penetrating amino acid sequences are in α-helix conformation. In different embodiment, at least 50%, or at least 60%, or at least 70% or at least 80% or at least 90% or at least 95% of the cell penetrating amino acid sequence is in an α-helix conformation.

The acronym "PEP" refers to E2F inhibitory penetratin-peptides as disclosed herein. PEP-1 refers to a peptide having the sequence of SEQ ID NO: 3 and PEP-2 refers a peptide having the sequence of to SEQ ID NO: 34.

Derivatives of all of the amino acid sequences discussed above are also encompassed by this invention. As used herein, the term "derivative", when used in the context of a peptide or polypeptide, means a peptide or polypeptide different other than in primary structure (amino acids and amino acid analogs). By way of illustration, derivatives may differ by being glycosylated, one form of post-translational modification. For example, peptides or polypeptides may exhibit glycosylation patterns due to expression in heterologous systems. If at least one biological activity is retained, then these peptides or polypeptides are derivatives according to the invention. Other derivatives include, but are not limited to, fusion peptides or fusion polypeptides having a covalently modified N- or C-terminus, PEGylated peptides or polypeptides, peptides or polypeptides associated with lipid moieties, alkylated peptides or polypeptides, peptides or polypeptides linked via an amino acid side-chain functional group to other peptides, polypeptides or chemicals, and additional modifications as would be understood in the art.

The cell-penetrating amino acid sequences and the peptides that bind consensus E2F recognition site may be fused immediately to each other or via linkers. In different embodiments, the peptide that binds consensus E2F recognition site may be fused either to N- or to C-terminus of the cell penetrating amino acid sequence.

The linkers or spacers are preferably relatively short (i.e., 1, 2, 3, 4, 5, 6, 7, 8, 9, or 10 amino acids), and preferably assume an α-helical conformation in cellular environment. The tools for determining protein conformation are well known in the art, and therefore, it is within the expertise of an ordinarily skilled artisan to predict what amino acids and/or amino acid sequences are suitable as linkers.

The amino acid sequence constructs of the instant invention may be produced by multiple methods. For example, one may chemically synthesize them, according to the methods well known in the art. The chemical synthesis method is particularly suitable if non-natural amino acids (e.g., D-amino acids) are used.

In other embodiments, these constructs may be recombinantly produced. It is within ordinary skill in the art to deduce nucleic acid sequences for the desired protein construct, optimize these sequences for the particular expression system used, insert these sequences into a vector, e.g., a plasmid or a viral vector, under control of the appropriate promoter, which may be selected based on the expression system used.

Once the nucleic acids encoding the amino acid construct of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including *E. coli*, other bacterial hosts, such as *Bacillus* or *Pseudomonas*, yeast, and various higher eukaryotic cells such as the COS, CHO, HeLa and myeloma cell lines. No attempt to describe in detail the various methods known for the expression of proteins in prokaryotes or eukaryotes will be made.

Briefly, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

In some cases, the amino acid constructs of the instant invention may need to be "refolded" and oxidized into a proper tertiary structure and possibly generating disulfide linkages in order to be biologically active. Refolding can be accomplished using a number of procedures well known in the art. Such methods include, for example, exposing the solubilized polypeptide agent to a pH usually above 7 in the presence of a chaotropic agent. The selection of chaotrope is similar to the choices used for inclusion body solubilization, however a chaotrope is typically used at a lower concentration. An exemplary chaotropic agent is guanidine. In most cases, the refolding/oxidation solution will also contain a reducing agent plus its oxidized form in a specific ratio to generate a particular redox potential which allows for disulfide shuffling to occur for the formation of cysteine bridges. Some commonly used redox couples include cysteine/cystamine, glutathione/dithiobisGSH, cupric chloride, dithiothreitol DTT/dithiane DTT, and 2-mercaptoethanol (bME)/dithiobME. In many instances, a co-solvent may be used to increase the efficiency of the refolding. Commonly used cosolvents include glycerol, polyethylene gluycol of various molecular weights, and arginine.

Protein purification techniques are also well known to those of skill in the art. These techniques involve, at one level, the crude fractionation of the proteinaceous and non-proteinaceous fractions. Having separated the construct of the instant invention from other proteins, the peptide or polypeptide of interest can be further purified using chromatographic and electrophoretic techniques to achieve partial or complete purification (or purification to homogeneity). Analytical methods particularly suited to the methods the present invention are ion-exchange chromatography, exclusion chromatography; polyacylamide gel electrophoresis; isoelectric focusing. A particularly efficient method of purifying peptides is fast protein liquid chromatography or even HPLC.

Once the amino acid construct of the instant invention is isolated and/or purified, it may be formulated according to known pharmaceutical principles taking into account, inter alia, the desired route of administration. It further may be advantageous to formulate the protein construct of the instant invention into a formulation which provides for longer stability and/or further improved cell penetration.

The degradation and stabilization of proteins in general has been well described in the literature, and the use of excipients such as dextran, lactose, sorbitol, mannitol, sucrose and trehalose as cryoprotectants and osmoregulators are well documented (see for example reviews of protein stability by Arakawa et al, Advanced Drug Delivery Reviews, 46, 307-326 (2001), Wang, et al., International Journal of Pharmaceutics 185, 129-188 (1999), and on trehalose by Crowe, et al., Cryobiology 43, 89-105 (2001)).

For example, in certain embodiments, the amino acid constructs of the instant invention may be PEGylated.

In another set of embodiments, the amino acid constructs of the instant invention may be encapsulated into liposomes, which, preferably, are PEGylated. PEGylated liposomal preparations would be expected to be more stable in Vivo and prolong the serum half life of the PEP. A suitable non-limiting example of PEGylated liposomes is provided below among the Examples.

Preferably, the amino acid construct formulated according to the description above exhibits an improved stability (i.e., longer half-life) as compared to the unformulated amino acid construct in physiological environment, including both intra- and extracellular environment. In different embodiments, the half-life may increase by at least tenfold. Thus, in certain embodiments, the half-life will increase by at least about 100%, or by at least about 200%, or by at least about 300% or by at least about 400%, or by at least about 500%, or by at least about 600% or by at least about 700% or by at least about 800% or by at least about 900% or by at least about 950%.

In another aspect, the amino acid sequences of the instant invention as disclosed above, may be used for a manufacture of a medicament for treatment of a malignant tumor, i.e., cancer.

In certain embodiments, the cancer is characterized by overexpression of E2F and/or the lack of expression of a functional retinoblastoma protein (pRb). The lack of expression of the functional retinoblastoma protein (pRb) is defined as a retention of no more than 50% of pRb function in non-cancerous cell of the same type. Thus, the definition encompasses situations where normal pRb is expressed at a level of less than 50%, or wherein the pRb is expressed, which retains only 50% of activity of wild-type pRb. Straightforward tests for determination of pRb amount and/or activity are known in the art (e.g., western blotting and sequencing). In one embodiment, the cancer is a hormone-refractory prostate cancer.

Other types of cancers characterized by these conditions may be selected from among solid tumors or liquid cancers. Solid tumors include, without limitations, brain cancer, lung cancer, stomach cancer, duodenal cancer, esophagus cancer, breast cancer, colon and rectal cancer, bladder cancer, kidney cancer, pancreatic cancer, prostate cancer, ovarian cancer, mouth cancer, eye cancer, thyroid cancer, urethral cancer, vaginal cancer, neck cancer, lymphoma, and the like. Other types of lung cancer include non-small cell lung cancer (NSCLC), small cell lung cancer, bronchioloalveolar carcinoma (BAC), squamous carcinoma and adenocarcinoma of the lung. In other embodiments, different cancers of blood cells are amenable to treatment. These blood cancers include, without limitations, Acute lymphocytic leukemia, Chronic myelogenous leukemia, Chronic lymphocytic leukemia, Hairy cell leukemia, myelomas and lymphomas.

In certain embodiments, the cancer is non-small cell lung cancer or malignant melanoma.

The amino acid sequences of the instant invention may be administered in conjunction with other beneficial agents, such as, for example, inhibitors of dihydrofolate reductase, thymidylate synthase and ribonucleotide reductase. Suitable non-limiting examples of such inhibitors include methotrexate, pralatrexed, aminopterin or 5-fluorouracil, fluorodeoxyuridine, pemetrexed, raltitrexed, or hydroxyurea. In the embodiments, where the cancer is a hormone refractory prostate cancer, the inhibitor may be taxotere or other effective agents.

The amino acid sequence(s) and/or the inhibitor(s) according to any embodiment described above may be present in the composition in different formulations including modified release formulations and/or nanoparticulate formulations. Examples of such formulations have been described in the art.

The advantages of the nanoparticulate formulation include an increased rate of dissolution in vitro, an increased rate of absorption in vivo, a decreased fed/fasted ratio variability, and a decreased variability in absorption.

The main advantage of the modified release formulations is that the drug or drugs are released according to the predetermined profile, thus eliminating the necessity of multiple administrations.

Suitable pharmaceutically acceptable carriers are well known to those skilled in the art. These include non-toxic physiologically acceptable carriers, adjuvants or vehicles for parenteral injection, for oral administration in solid or liquid form, for rectal administration, nasal administration, intramuscular administration, subcutaneous administration, and the like.

Depending on the nature of the cancer, the amino acid sequences of the instant invention and the inhibitor(s) may be administered by routes independently selected from the group consisting of oral administration, intravenous administration, intraarterial administration, intramuscular administration, intracolonic administration, intracranial administration, intrathecal administration, intraventricular administration, intraurethral administration, intravaginal administration, subcutaneous administration, intraocular administration, intranasal administration, and any combinations thereof.

In different embodiments, the amino acid sequences of the instant invention may be administered before, simultaneously with, or after the inhibitor. Simultaneous administration assumes that all of the compounds are administered within one hour (e.g., 45 minutes, 30 minutes, 20 minutes, 10 minutes, 5 minutes, 1 minute, at the same time) of each other.

The administration of the amino acid sequences of the instant invention before the inhibitor(s) of the instant invention assumes that the administration of inhibitor(s) ends within 72 hours after the administration of the amino acid sequence(s) begins.

The administration of the amino acid sequences of the instant invention after the inhibitor(s) of the instant invention assumes that the administration of the amino acid sequence(s) ends within 72 hours after the administration of the inhibitor(s) begins.

Thus, in different embodiments, the aforementioned time period is less than about 60 hours, less than about 48 hours, less than about 36 hours, less than about 24 hours, less than about 16 hours, less than about 8 hours, less than about 4 hours, less than about 3 hours, or less than about 2 hours.

The invention will now be described in the following non-limiting examples.

EXAMPLES

Example 1

Generation of an E2F-1 Inhibitory Peptide

The inventors have utilized a phage display library to screen a relatively small random peptide combinatorial library (heptamer library) to identify peptides that may bind to DNA at consensus E2F binding sites and thereby interfere with the binding of native E2F protein. Phage display was used to find heptapeptides that bound tightly to an immobilized consensus E2F sequence, shown below (in bold).

```
                                          (SEQ ID NO: 5)
5'ATT TAA GTT TCG CGC CCT TTC TCA A-3'

(SEQ ID NO: 6)
3'TAA ATT CAA AGC GCG GGA AAG AGT-T-5'
```

The phage display library contained random peptides fused to the N terminus of the minor coat protein (pIII) of M13 separated by a Gly-Gly-Gly-Ser (SEQ ID NO: 22) spacer. The bait was a 3' biotinylated 17 bp double stranded oligomer which contained the inverted repeat of the consensus E2F binding site from the human DHFR promoter. Streptavidin coated polystyrene petri dishes (60×15 mm) were used for trapping the biotinylated 17 bp oligomer (the bait) and $2 \times 10^{13}$ pfu from the phage library was added to the dish. The specifically bound phage particles were eluted and two further rounds of amplification of the eluted phage was carried out leading to a 10,000 fold enrichment. The eluates from round three were processed for isolation and sequencing of DNA, without further amplification to avoid spontaneous mutations.

After stringent washing conditions, 8 phage clones were isolated, and the DNA sequenced. The peptides in those clones were as follows: His HisHisArgLeuSerHis (SEQ ID NO: 1, in five clones), HisArgProTrpIleAlaHis (SEQ ID NO: 7), HisAlaIleTyrProArgHis (SEQ ID NO: 8), ProGluTyrAsp-ProTyrPhe (SEQ ID NO: 9). As SEQ ID NO: 1 appeared in 5 of the 8 tight binding peptides, this peptide was selected for further study.

Example 2

The Peptide Coupled to Penetratin (PEP-1) Inhibits Growth of Many but Not all Human Cancer Cell Lines The cells cultured in RPMI media and 10% fetal calf serum were treated with various concentrations of SEQ ID NO: 3 or SEQ ID NO: 19 at various concentrations for 24 hours and cell viability was determined using Vi-CELL automated cell counter.

Figure 1B:
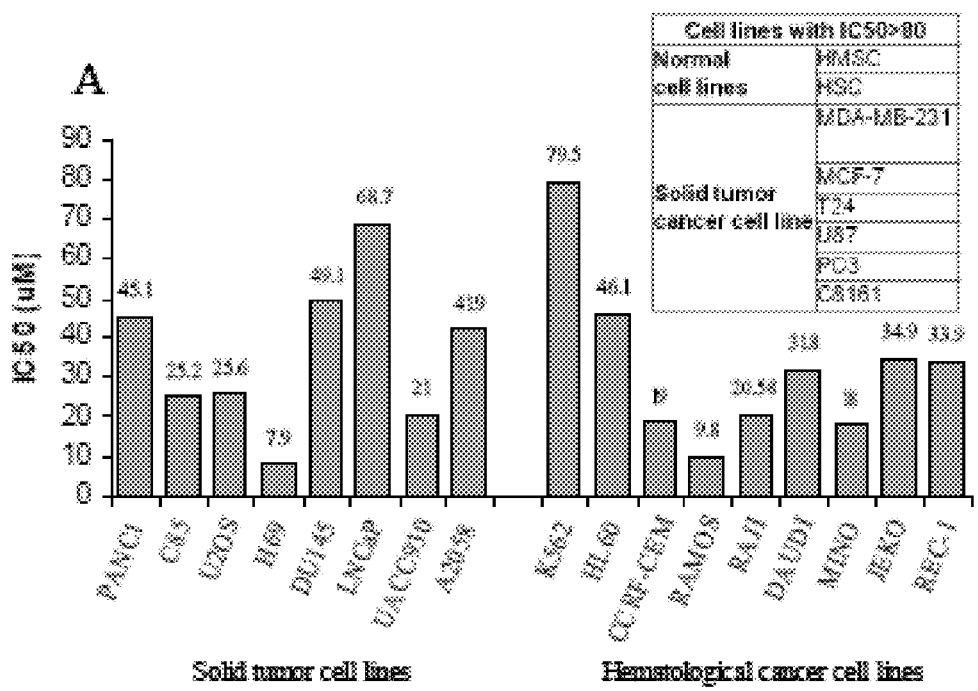

The free peptide did not inhibit growth of several tumor cell lines tested, and likely was not taken up by the cells. However, when coupled to penetratin (SEQ ID NO: 2). As shown in FIG. 1A, the peptide was found to be cytotoxic to most, but not all, tumor cell lines, with variable effectiveness (FIG. 1B). A control peptide, with all 4 of the histidines replaced by alanines (see FIG. 1A), had little or no effect on cell growth at comparable PEP concentrations (data not shown). Importantly, normal human CD34 positive cells containing hematopoeitic progenitors (HSC) were relatively insensitive to the PEP (IC50>80 μM), as were marrow mesenchymal stem cells (HMSC) and primary mouse fibroblasts (MEFs). The Ramos (Burkitt lymphoma) cell line and the H69 (small cell lung cancer) cell lines had the lowest IC50 values.

As the H69 cell line was found to have high levels of "free" E2F-1, related to lack of pRB (Li et al, 1995) the effect of pRB was studied the H865 small cell lung cancer cell line that contains a functional pRb.

Figure 2:
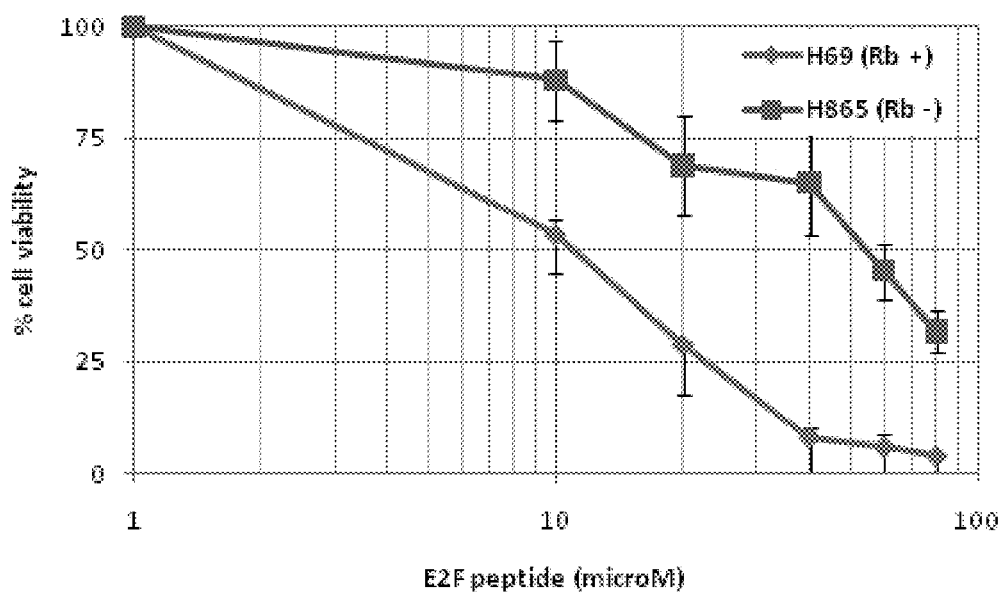
FIG. 2 is an illustration of the effect of the E2F inhibitory penetratin-peptide on viability of Rb positive H69 and Rb negative small lung cancer cell lines.

As shown in FIG. 2, the H69 cell line was more sensitive to the PEP-1 compared to the H865 cell line. While this does not prove that the presence or lack of functional pRB affects sensitivity, additional experiments are now in progress with the H69 cell line transfected with pRB (Budak-Alpdogan, 2007) to determine if cells lacking functional pRB are generally more sensitive to PEP-1. Of interest, the Ramos and H69 cell lines also had high levels of E2F-1 as measured by Western blotting. Experiments are now in progress to determine a possible correlation between E2F-1, -2, and -3 levels and sensitivity to PEP-1 in multiple cell lines.

Example 3

Cell Death During PEP-1 Exposure

To determine the mechanism of cell death by PEP-1, DU 145 cells cultured as described above were incubated with the PEP (50 micromolar) for 4 and 24 hours and analyzed for Annexin V and PI staining by flow cytometry (n=3). Annexin V stained cells represents early apoptotic cells, and PI+Annexin V double staining and PI alone staining indicate late apoptosis and necrotic cells.

Figure 3:
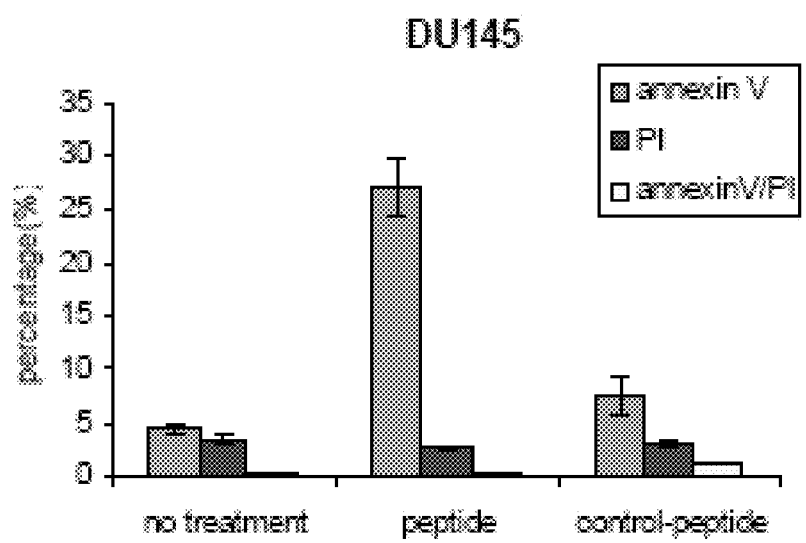
FIG. 3 demonstrates induction of apoptosis by PEP in DU145 cells.

Cells underwent apoptosis following as little as a 4 hour exposure (FIG. 3). Similar results were obtained in Ramos cell line (not shown).

Example 4

PEP-1 Downregulates E2F-1 mRNA Expression and Important Downstream Targets: DHFR, TS, TK, and RR-2.

E2F-1 is known to enhance its own transcription and that of other activating E2Fs as well as genes required for S-phase, including DHFR, TS, TK, and RR-2.

To assess effects of PEP-1 on several downstream proteins, DU145 cells were treated with different concentrations of SEQ ID NO: 3 or SEQ ID NO: 19. Western-blotting was performed with antibody against the indicated E2F protein targets 24 hours after the treatment. RT-PCR analysis on total RNA was carried 8 hours after treatment using the following primers:

```
                                            (SEQ ID NO: 23)
E2F-1 Fwd 5'-AGGCTGGACCTGGAAACTGACCAT-3'

(SEQ ID NO: 24)
E2F-1 Rev 5'-AGCTGCGTAGTACAGATATTCATCA-3'

(SEQ ID NO: 25)
TK Fwd 5'-GCATTAACCTGCCCACTGTGCTGC-3'

(SEQ ID NO: 26)
TK Rev 5'-GTGCCGAGCCTCTTGGTATAGGC-3'

(SEQ ID NO: 27)
TS Fwd 5'-GCGCTACAGCCTGAGAGATGAATT-3'

(SEQ ID NO: 28)
TS Rev 5'-CTTCTGTCGTCAGGGTTGGTTTTG-3'

(SEQ ID NO: 29)
RR-2 Fwd 5'-TGGAGGATGAGCCGCTGCTGAGA-3'

(SEQ ID NO: 30)
RR-2 Rev 5'-TTGACACAAGGCATCGTTTCAATGG-3'
```

Figure 4:
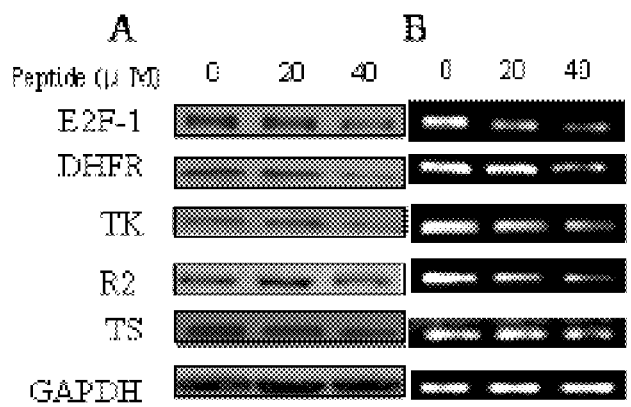
FIG. 4 demonstrates downregulation of E2F-1, DHFR, TK, R2, and TS levels by PEP on protein level (FIG. 4A) and mRNA level (FIG. 4B).

FIG. 4 demonstrates that E2F-1, TS, TK, and RR-2 protein (FIG. 4A) and mRNA (FIG. 4B) are down regulated in the presence of the peptide.

Example 5

PEP-1 Specifically Down Regulated E2F-1

Serum-starved DU145 cells were treated with the PEP or control peptide for 24 hours. A ChiP assay was performed with an antibody against E2F-1 and control IgG. The primers used for PCR flanked the two E2F-1 binding sites in the E2F1 promoter. The sequences for the primers were as follows:

```
                                            (SEQ ID NO: 31)
Fwd 5'-AGGAACCGCCGCCGTTGTTCCCGT-3'

(SEQ ID NO: 32)
Rev 5'-CTGCCTGCAAAGTCCCGGCCACTT-3'
```

Figure 5:
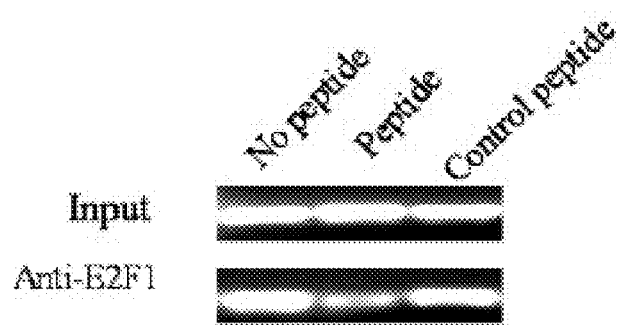
FIG. 5 demonstrates that the PEP inhibits E2F1 protein binding to its promoter.

As shown in FIG. 5, PEP-1 (but not the control peptide of SEQ ID NO: 19) entered the cells and bound to the E2F-1 promoter, thus competing with E2F-1. Further studies are show that the PEP also down regulates E2F-2 and E2F-4, as well as E2F-1, indicating that the cytotoxic effects of the Pep may not be restricted to only down regulating E2F-1.

Example 6

Combination Studies with PEP-1 and MTX

Figure 6:
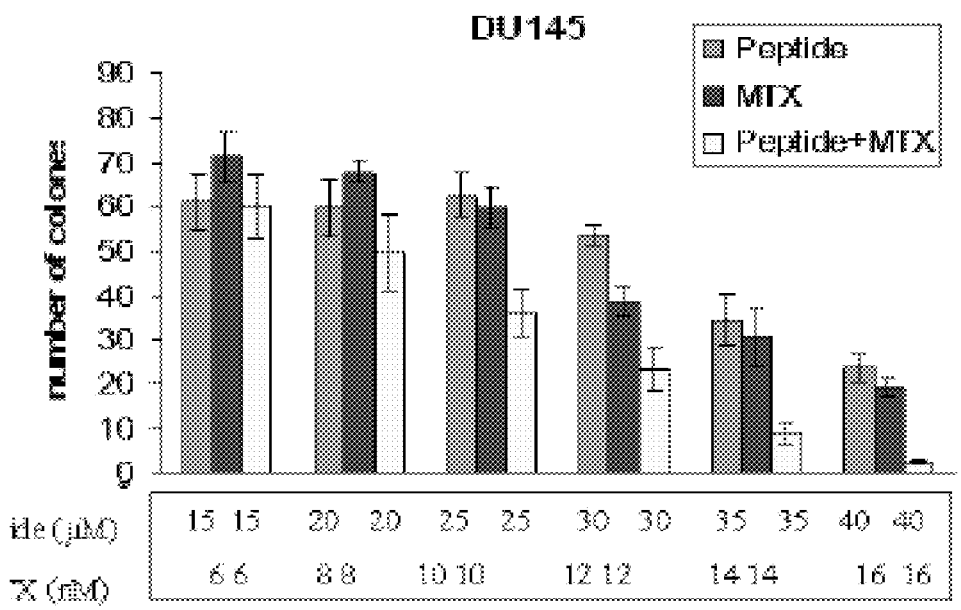
FIG. 6 illustrates a synergistic effect of SEQ ID NO: 3 and MTX on viability of DU145 cells.

Two hundred DU145 cells were seeded in plates. E2F peptide and MTX were added at various concentrations. After 2 weeks, colonies were counted and data were analyzed. In this study, the PEP-1-MTX combination showed synergy at the highest concentration of both agents (FIG. 6) (CI<1 by Chou-Talaly analysis).

These results, together with the Western analysis, supports the proposition that down regulation of key enzyme targets by PEP-1 may enhance the cytotoxicity of drugs that target these enzymes.

Example 7

PEP-1 is Relatively Unstable in Cell Culture Media

The IC50 values shown above (see, e.g., Example 2) were obtained after a single 24 h exposure to PEP-1; additional exposure times did not increase potency. This result indicated that the peptide was probably not stable in the media containing FBS. This was confirmed by incubating the peptide in cell-free media and FBS for 24 h, then adding cells and assaying cytotoxicity. Under these conditions there was a marked decrease in cytotoxicity (data not shown).

Adding fresh peptide every 24 hours to DU145 cells increased potency (FIG. 7), as determined by the calculation of percentage of viable cells (by trypan blue staining) collected at day 3. These data confirm that PEP-1 was relatively unstable in RPMI media and FBS.

Example 8

Preparation of PEGylated Liposomes Containing PEP-1

To increase stability of PEP-1 for in vivo studies, PEGylated liposomes were prepared as previously described (Pakunlu et al, 2004; Wang et al, 2008; Garbuzenko et al, 2009). Briefly, Egg phosphatidylcholine (EPC), cholesterol (Chol) and 1,2,-distearoyl-sn-glycero-3-phosphoethanolamine-N-aminopolyethylene glycol Mw—2000 ammonium salt (DSPE-PEG) purchased from Avanti Polar Lipids (Alabaster, Ala.), were dissolved in chloroform, evaporated to a thin film layer using a rotary evaporator ROTAVAPOR® R-210/R-215 (BUCHI Corp., New Castle, Del.) and rehydrated with 0.9% NaCl to final lipid concentration of 20 mM. The lipid mole ratio for this formulation was 51:44:5 EPC: Chol: DSPE-PEG respectively. PEP-1 (labeled with fluoroescein isothiocyanate (FITC), purchased from Bio Basin Inc (Ontario Cananda) was loaded into liposomes by dissolving in rehydration buffer at a concentration of 20 mM. Liposomes were stored at room temperature for an hour followed by extrusion through polycarbonate membranes (200 nm and 100 nm) using the extruder device (Northern Lipids Inc., Vancouver, BC, Canada). Free peptide was separated from liposomes by dialysis using dialysis membrane with a pore size of 12-14 kDa (Spectrum Labs, Houston, Tex.) against 100 volumes of 0.9% NaCl overnight. Liposomes were characterized by assessing their size and charge by dynamic light scattering and zeta-potential measurements, respectively. The liposomes were neutral with an average size of 100 nm.

Typical images of DU145 human prostate cancer cells incubated with PEGylated liposomes containing E2F1 peptide are provided in FIG. 8. Cell nuclei were stained with nuclear-specific dye DAPI, PEP-1 was labeled with FITC. Superimposition of images allows for detecting of cytoplasmic and nuclear localization of peptide. The inventors have found that FITC PEP-1 encapsulated liposomes were taken up within 5 min and entered the nucleus.

Example 9

Molecular Model of Interaction of Peptides of the Instant Invention with DNA E2F Promoter Region To explore important structural motifs in E2F1 required for selectivity in binding to DNA in humans, we needed a model of the protein-DNA complex based on the human sequence. The homology model was built using the Modeller (9v5) program (Sali and Blundell 1993; Marti-Renom, Stuart et al. 2000; Sanchez and Sal12000; Marti-Renom, Madhusudhan et al. 2002). The DNA binding domains of the E2F1 and DP1 sequences (NCBI accession #'s AAC50719 and NP009042 respectively) were used for modeling the E2F1-DP1 transcription factor complex with DNA. A single template approach was employed using the x-ray crystal structure of the human E2F4-DP2 complex with DNA (1CF7.pdb) as the template structure (Zheng, Fraenkel et al. 1999).

The DNA from the crystal structure was modeled in place using the default spatial constraints in the Modeller program. The E2F1-DP1 heterodimer winged helix fold places the helices of the two proteins in the major groove of the DNA. The conserved RRXYD motif (SEQ ID NO: 21, wherein "X" is isoleucine or valine or conservative substitutions of these amino acids) found in the helices of E2F-1 and DP1 is important for DNA recognition. The relevant portions of E2F proteins are demonstrated below:

E2F1
SEQ ID NO: 10
RFLELLSHSADGVVDLNWAAEVLKVQ-K*RRIYD*ITNVLEGIQLIAKKSKN

E2F2
SEQ ID NO: 11
KFIYLLSESEDGVLDLNWAAEVLDVQ-K*RRIYD*ITNVLEGIQLIRKKAKN

E2F3
SEQ ID NO: 12
KFIQLLSQSPDGVLDLNKAAEVLKVQ-K*RRIYD*ITNVLEGIHLIKKKSKN

E2F4

-continued
SEQ ID NO: 13
KFVSLLQEAKDGVLDLKLAADTLAVRQK*RRIYD*ITNVLEGIGLIEKKSKN

E2F5
SEQ ID NO: 14
KFVSLLQEAKDGVLDLKAAADTLAVRQK*RRIYD*ITNVLEGIDLIEKKSKN

E2F6
SEQ ID NO: 15
KFMDLVRSAPGGILDLNKVATKLGVR-K*RRVYD*ITNVLDGIDLVEKKSKN

Using the methodology described above, the direct hydrogen bonding interactions between the arginine residues and the DNA bases (a very polar environment requiring polar residues like arginine, lysine and histidine for efficient binding) are predicted.

The leading candidate (SEQ ID NO: 1), having four positively charged amino acids fits this model. This sequence was fused with SEQ ID NO: 2, thereby creating SEQ ID NO: 3. Negative control sequences (GGGALSA, SEQ ID NO: 16 and AAAVLSA, SEQ ID NO: 17) were fused to SEQ ID NO: 2 in a similar manner, i.e., immediately to the C-terminus of SEQ ID NO: 2, thus resulting in SEQ ID NOs 18 and 19, respectively. Notably, SEQ ID NOs: 16 and 17 are relatively non-polar peptides, as compared to SEQ ID NO: 1. SEQ ID NOs 1, 16, 17, 3, 18, and 19 were docked to a model of the following DNA sequence built as the B-form using the Amber nucleic acid builder (Macke and Case 1998): 5'-AGTTTG-GCGCGAAAT-3' (SEQ ID NO: 20) as a double helix with its complement. The penetratin-linked peptides (PEPs) (e.g. SEQ ID NO: 3) were built from 9ANT.pdb (template) (Fraenkel and Pabo 1998) using the Modeller program. The small peptides of SEQ ID NOs 1, 16, and 17 were built using the Maestro molecular graphics package (Schrödinger Software). All peptide models were pre-equilibrated in a water box at 300 K and 1 atm for 6 ns using the Amber 10 biomolecular simulation programs (Case, Cheatham III et al. 2005) prior to docking. Docking of the peptides to DNA was performed based on shape similarity using the PatchDock program (Schneidman-Duhovny, Inbar et al. 2005; Schneidman-Duhovny, Inbar et al. 2005). The resulting top ten hits of each docking was re-scored using simple interaction energies (Eint=ΣEvdw+ΣEelec) with infinite non-bonded cutoffs based on the Amber 99SB forcefield (Hornak, Abel et al. 2006). Estimates of thermodynamic properties including $\Delta G_{bind}$ for the complexes was computed from molecular dynamics trajectories in a water box for each complex using the MM-PBSA/GBSA routines in the Amber 10 biomolecular simulation software package. Estimates of the entropy values were computed using the nucleic acid builder (Macke, T. and D. A. Case (1998); Leontes and SantaLucia, (1998) and DNA axis bend calculated using the Curves+software package (Layery, et al. (2009).

TABLE 1

Estimates of thermodynamic properties (kcal/mol) and DNA helical axis bend for the penetratin linked peptides. T = 300 K

| SEQ ID | EPB (kcal/mol) | $E_{GB}$ (kcal/mol) | −TΔS (kcal/mol) | ΔGbind (PBSA) | ΔGbind (GBSA) | Helical Bend (deg)† |
|---|---|---|---|---|---|---|
| 19 | −63.3 ± 7.6 | −39.9 ± 7.5 | +32.3 ± 6.5 | −31.0 ± 10.0 | −7.6 ± 9.9 | 27.5° |
| 18 | −75.2 ± 7.5 | −62.8 ± 8.5 | +54.4 ± 3.8 | −20.8 ± 8.4 | −8.4 ± 9.3 | 4.3° |
| 3 | −99.5 ± 11.1 | −79.0 ± 12.0 | +53.1 ± 4.7 | −46.4 ± 12.1 | −25.9 ± 13.0 | 27.9° |

†Note: Helical bend of DNA in 1CF7.pdb is equal to 7.3°

The best scores from this analysis indicate the alpha helical portion of SEQ ID NO: 2 greatly enhances binding of SEQ ID NO: 1 and SEQ ID NO: 16 in the context of respective SEQ ID NOs 3 and 18. The curvature of SEQ ID NO: 3 makes a nice fit into the DNA major groove and the abundance of basic residues in SEQ ID NO: 1 interact very well with the bases and phosphate backbone of the DNA. SEQ ID NO: 18 lacks curvature and has fewer interactions with the DNA. Thus SEQ ID NO: 3 is predicted to interact with DNA better than SEQ ID NO: 18 or 19. The helical bend of the DNA in the crystal structure of the E2F4-DP2 complex is small)(7.3° compared to the bend found in SEQ ID NO:3 complex) (27.9°. DNA bending may play a role in blocking the transcription factor binding.

Example 10

PEP-2 Decreases the Size of Tumors in Vivo

Figure 10:
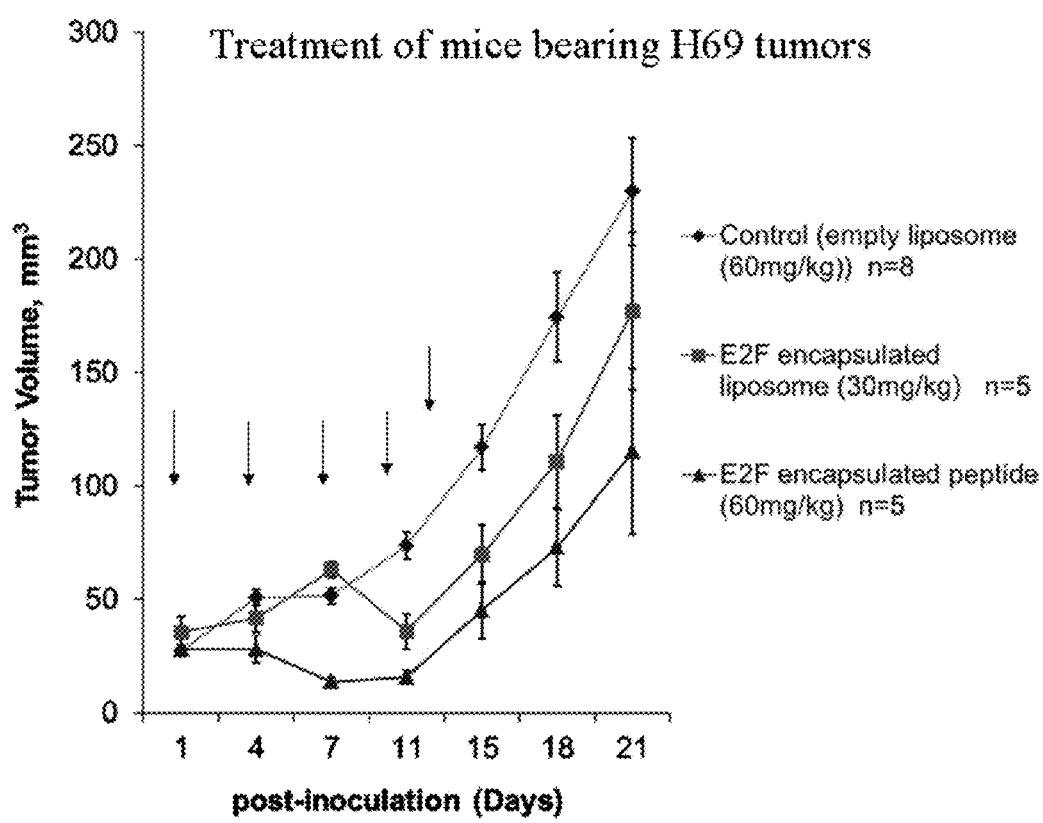
FIG. 10 is an illustration of the effect of PEP-2, (E2F inhibitory penetratin-peptide) on mice bearing H69 tumors.
Figure 11:
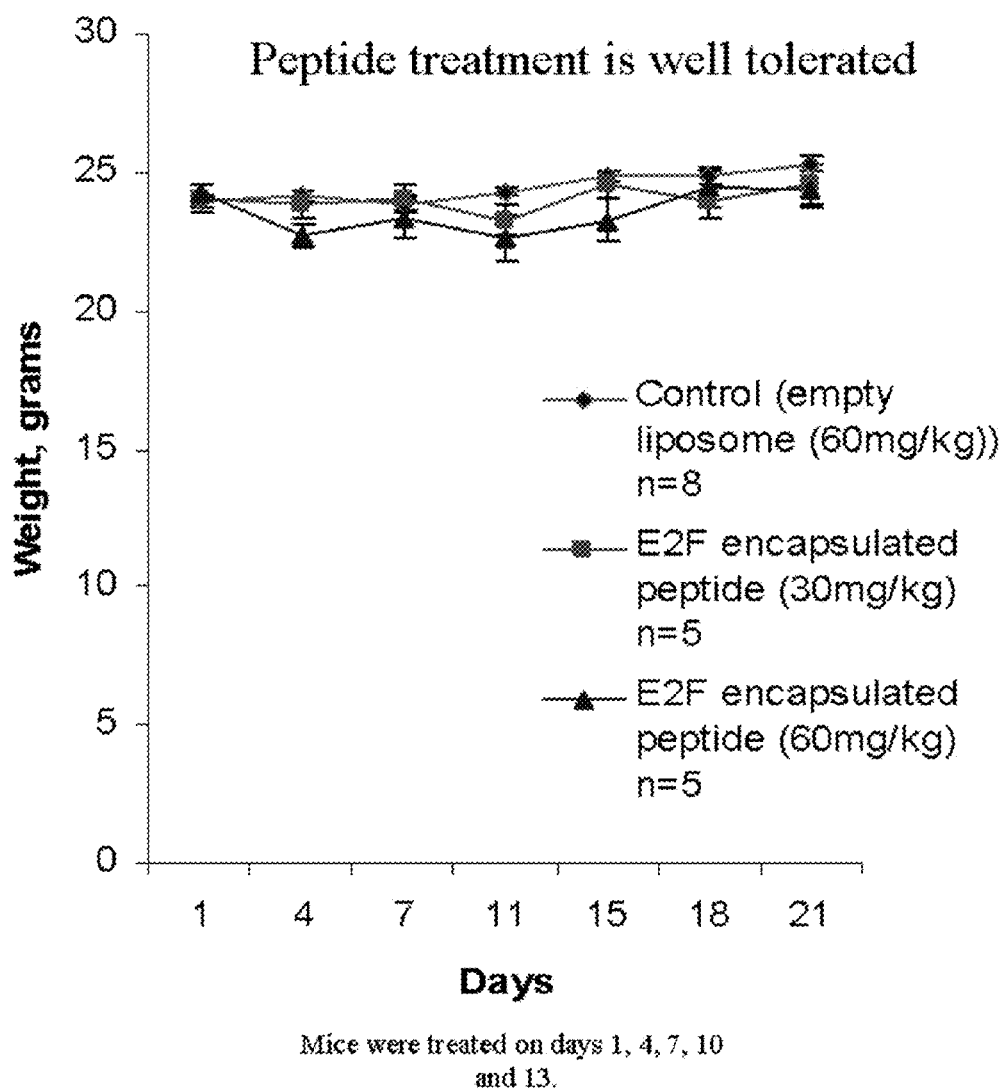
FIG. 11 is an illustration that the treatment of mice with PEP-2 (E2F inhibitory penetratin-peptide) is tolerated.
Figure 12:
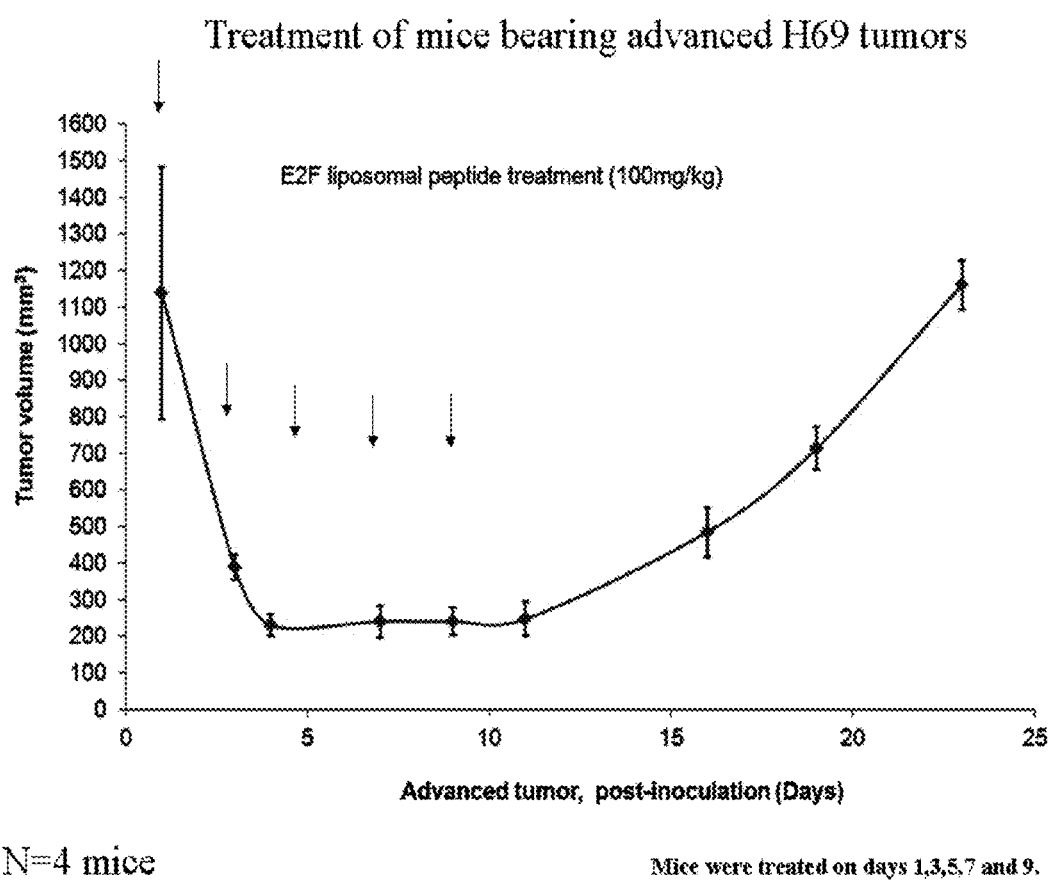
FIG. 12 is an illustration of the effect of PEP-2 (E2F inhibitory penetratin-peptide) on mice bearing advanced H69 tumors.
Figure 13:
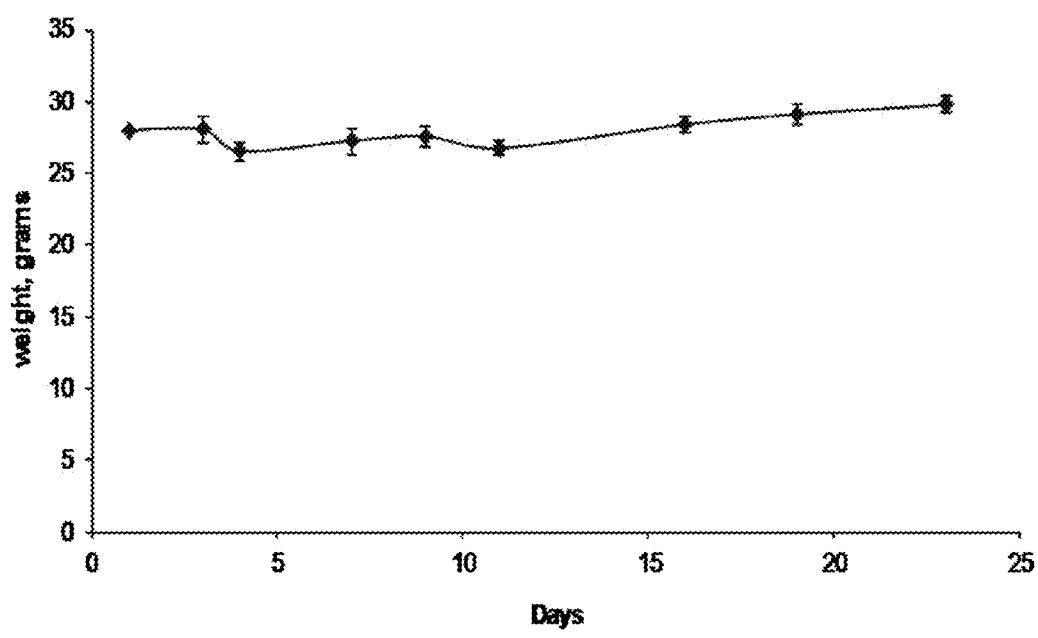
FIG. 13 is an illustration that treatment of mice bearing advanced tumors with encapsulated PEP-2 (E2F inhibitory penetratin-peptide) is tolerated.

Nude mice bearing the H-69 small cell carcinoma xenografts were treated with PEP-2 encapsulated in PEGylated liposomes as previously described. Female mice (20-22 g) were inoculated intraperitoneally with 10 million tumor cells suspended in 50 uL of PBS and an equal volume of matrigel. When the tumors were approximately 50 mm 3, the animals were randomized into groups of 6 and either treated with 0.06 ml of empty PEGylated liposomes, or 0.03 ml of PEGylated liposomes (30 mg/kg of PEP-2) or 0.06 ml of PEGylated liposomes (60 mg/kg of PEP-2), every 4 days. Tumor size (FIG. 10) and animal weight (FIG. 11) was measured every three days. The 60 mg/kg dose produced acute transient distress, likely due to liposome trapping in the lungs; all animals recovered quickly, and subsequent doses had less of an effect. Treatment of mice bearing advanced Tumors (FIG. 12) and mice with advanced tumors tolerate the encapsulated PEP-2 liposome treatment (FIG. 13).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

All patent and non-patent publications cited in this specification are indicative of the level of skill of those skilled in the art to which this invention pertains. All these publications and patent applications are herein incorporated by reference to the same extent as if each individual publication or patent application was specifically and individually indicated to be incorporated herein by reference.

The invention claimed is:

1. A method of treating a patient diagnosed with a malignant tumor expressing E2F-1 comprising administering to the patient a peptide having an amino acid sequence consisting essentially of RQIKIWFQNRRIKWKKHHHRLSH(SEQ ID NO: 34), wherein the peptide is encapsulated within a liposome, or a formulation comprising a peptide having an amino acid sequence consisting essentially of RQIKIWFQNRRIK-WKKHHHRLSH(SEQ ID NO: 34), and a pharmaceutically acceptable carrier in an amount effective to inhibit the growth of the tumor.

2. The method of claim 1, further comprising administering to said malignant tumor an inhibitor of thymidylate synthase and ribonucleotide reductase.

3. The method of claim 2 wherein the inhibitor is methotrexate or 5-fluorouracil.

4. The method of claim 1, wherein said malignant tumor is a cancer selected from the group consisting of brain cancer, lung cancer, stomach cancer, duodenal cancer, esophagus cancer, breast cancer, colon and rectal cancer, bladder cancer, kidney cancer, pancreatic cancer, prostate cancer, ovarian cancer, month cancer, eye cancer, thyroid cancer, urethral cancer, vaginal cancer, neck cancer, and lymphoma.

5. The method of claim 1, wherein said malignant tumor is characterized by a lack of expression of a functional retinoblastoma protein (pRb).

6. The method of claim 1, wherein the peptide RQIKIW-FQNRRIKWKKHHHRLSH (SEQ ID NO: 34) is encapsulated within a liposome.

7. The method of claim 1, wherein the liposome is PEGylated.

8. A method of treating a patient diagnosed with a malignant tumor expressing E2F-1 comprising administering to the patient a peptide having an amino acid sequence consisting essentially of RQIKIWFQNRRIKWKICHHHRLSH (SEQ ID NO: 34), wherein the peptide comprises at least one D-amino acid within the HHHRLSH region.

9. The method of claim 7, wherein said malignant tumor is a cancer selected from the group consisting of brain cancer, lung cancer, stomach cancer, duodenal cancer, esophagus cancer, breast cancer, colon and rectal cancer, bladder cancer, kidney cancer, pancreatic cancer, prostate cancer, ovarian cancer, mouth cancer, eye cancer, thyroid cancer, urethral cancer, vaginal cancer, neck cancer, and lymphoma.

10. The method of claim 4, wherein said prostate cancer is a hormone refractory prostate cancer.

11. The method of claim 4, wherein said lune cancer is a small cell lung cancer.

\* \* \* \* \*

```
SEQUENCE LISTING

<160> NUMBER OF SEQ ID NOS: 34

<210> SEQ ID NO 1
<211> LENGTH: 7
<212> TYPE: PRT
<213> ORGANISM: Artificial
<220> FEATURE:
<223> OTHER INFORMATION: synthetic oligopeptide

<400> SEQUENCE: 1

His His His Arg Leu Ser His
1               5

<210> SEQ ID NO 2
<211> LENGTH: 16
<212> TYPE: PRT
<213> ORGANISM: Artificial
<220> FEATURE:
<223> OTHER INFORMATION: synthetic oligopeptide

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 23
<212> TYPE: PRT
<213> ORGANISM: Artificial
<220> FEATURE:
<223> OTHER INFORMATION: experimental penetratin peptide

<400> SEQUENCE: 3

Arg Gln Ile Lys Ile Trp Phe Gln Asn Arg Arg Met Lys Trp Lys Lys
1               5                   10                  15

His His His Arg Leu Ser His
            20

<210> SEQ ID NO 4
<211> LENGTH: 8
<212> TYPE: DNA
<213> ORGANISM: Artificial
<220> FEATURE:
<223> OTHER INFORMATION: E2F-1 promoter
<220> FEATURE:
<221> NAME/KEY: misc_feature
<222> LOCATION: (4)..(5)
<223> OTHER INFORMATION: n may be C or G

<400> SEQUENCE: 4 tttnncgc                                                            8
```

```
<210> SEQ ID NO 5
<211> LENGTH: 25
<212> TYPE: DNA
<213> ORGANISM: Artificial
<220> FEATURE:
<223> OTHER INFORMATION: consensus E2F sequence

<400> SEQUENCE: 5
atttaagttt cgcgcccttt ctcaa                                              25

<210> SEQ ID NO 6
<211> LENGTH: 25
<212> TYPE: DNA
<213> ORGANISM: Artificial
<220> FEATURE:
<223> OTHER INFORMATION: consensus E2F sequence

<400> SEQUENCE: 6
taaattcaaa gcgcgggaaa gagtt                                              25

<210> SEQ ID NO 7
<211> LENGTH: 7
<212> TYPE: PRT
<213> ORGANISM: Artificial
<220> FEATURE:
<223> OTHER INFORMATION: synthetic oligopeptide

<400> SEQUENCE: 7

His Arg Pro Trp Ile Ala His
1               5

<210> SEQ ID NO 8
<211> LENGTH: 7
<212> TYPE: PRT
<213> ORGANISM: Artificial
<220> FEATURE:
<223> OTHER INFORMATION: synthetic oligopeptide

<400> SEQUENCE: 8

His Ala Ile Tyr Pro Arg His
1               5

<210> SEQ ID NO 9
<211> LENGTH: 7
<212> TYPE: PRT
<213> ORGANISM: Artificial
<220> FEATURE:
<223> OTHER INFORMATION: synthetic oligopeptide

<400> SEQUENCE: 9

Pro Glu Tyr Asp Pro Tyr Phe
1               5

<210> SEQ ID NO 10
<211> LENGTH: 49
<212> TYPE: PRT
<213> ORGANISM: Artificial
<220> FEATURE:
<223> OTHER INFORMATION: E2F1 fragment

<400> SEQUENCE: 10

Arg Phe Leu Glu Leu Leu Ser His Ser Ala Asp Gly Val Val Asp Leu
1               5                   10                  15

Asn Trp Ala Ala Glu Val Leu Lys Val Gln Lys Arg Arg Ile Tyr Asp
            20                  25                  30
```

Ile Thr Asn Val Leu Glu Gly Ile Gln Leu Ile Ala Lys Lys Ser Lys
                35                  40                  45

Asn

<210> SEQ ID NO 11
<211> LENGTH: 49
<212> TYPE: PRT
<213> ORGANISM: Artificial
<220> FEATURE:
<223> OTHER INFORMATION: E2F1 fragment

<400> SEQUENCE: 11

Lys Phe Ile Tyr Leu Leu Ser Glu Ser Glu Asp Gly Val Leu Asp Leu
1               5                   10                  15

Asn Trp Ala Ala Glu Val Leu Asp Val Gln Lys Arg Arg Ile Tyr Asp
            20                  25                  30

Ile Thr Asn Val Leu Glu Gly Ile Gln Leu Ile Arg Lys Lys Ala Lys
                35                  40                  45

Asn

<210> SEQ ID NO 12
<211> LENGTH: 49
<212> TYPE: PRT
<213> ORGANISM: Artificial
<220> FEATURE:
<223> OTHER INFORMATION: E2F1 fragment

<400> SEQUENCE: 12

Lys Phe Ile Gln Leu Leu Ser Gln Ser Pro Asp Gly Val Leu Asp Leu
1               5                   10                  15

Asn Lys Ala Ala Glu Val Leu Lys Val Gln Lys Arg Arg Ile Tyr Asp
            20                  25                  30

Ile Thr Asn Val Leu Glu Gly Ile His Leu Ile Lys Lys Lys Ser Lys
                35                  40                  45

Asn

<210> SEQ ID NO 13
<211> LENGTH: 50
<212> TYPE: PRT
<213> ORGANISM: Artificial
<220> FEATURE:
<223> OTHER INFORMATION: E2F1 fragment

<400> SEQUENCE: 13

Lys Phe Val Ser Leu Leu Gln Glu Ala Lys Asp Gly Val Leu Asp Leu
1               5                   10                  15

Lys Leu Ala Ala Asp Thr Leu Ala Val Arg Gln Lys Arg Arg Ile Tyr
            20                  25                  30

Asp Ile Thr Asn Val Leu Glu Gly Ile Gly Leu Ile Gly Lys Lys Ser
                35                  40                  45

Lys Asn
    50

<210> SEQ ID NO 14
<211> LENGTH: 50
<212> TYPE: PRT
<213> ORGANISM: Artificial
<220> FEATURE:
<223> OTHER INFORMATION: E2F1 fragment

<400> SEQUENCE: 14

Lys Phe Val Ser Leu Leu Gln Glu Ala Lys Asp Gly Val Leu Asp Leu
1               5                   10                  15

Lys Ala Ala Ala Asp Thr Leu Ala Val Arg Gln Lys Arg Arg Ile Tyr
                20                  25                  30

Asp Ile Thr Asn Val Leu Glu Gly Ile Asp Leu Ile Glu Lys Lys Ser
                35                  40                  45

Lys Asn
    50

<210> SEQ ID NO 15
<211> LENGTH: 49
<212> TYPE: PRT
<213> ORGANISM: Artificial
<220> FEATURE:
<223> OTHER INFORMATION: E2F1 fragment

<400> SEQUENCE: 15

Lys Phe Met Asp Leu Val Arg Ser Ala Pro Gly Gly Ile Leu Asp Leu
1               5                   10                  15

Asn Lys Val Ala Thr Lys Leu Gly Val Arg Lys Arg Arg Val Tyr Asp
                20                  25                  30

Ile Thr Asn Val Leu Asp Gly Ile Asp Leu Val Glu Lys Lys Ser Lys
                35                  40                  45

Asn

<210> SEQ ID NO 16
<211> LENGTH: 7
<212> TYPE: PRT
<213> ORGANISM: Artificial
<220> FEATURE:
<223> OTHER INFORMATION: Negative control sequence

<400> SEQUENCE: 16

Gly Gly Gly Ala Leu Ser Ala
1               5

<210> SEQ ID NO 17
<211> LENGTH: 7
<212> TYPE: PRT
<213> ORGANISM: Artificial
<220> FEATURE:
<223> OTHER INFORMATION: Negative control sequence

<400> SEQUENCE: 17

Ala Ala Ala Val Leu Ser Ala
1               5

<210> SEQ ID NO 18
<211> LENGTH: 22
<212> TYPE: PRT
<213> ORGANISM: Artificial
<220> FEATURE:
<223> OTHER INFORMATION: negative control penetratin-linked peptide

<400> SEQUENCE: 18

Arg Gln Ile Lys Ile Trp Phe Gln Asn Arg Met Lys Trp Lys Lys Gly
1               5                   10                  15

Gly Gly Ala Leu Ser Ala
            20

```
<210> SEQ ID NO 19
<211> LENGTH: 23
<212> TYPE: PRT
<213> ORGANISM: Artificial
<220> FEATURE:
<223> OTHER INFORMATION: negative control penetratin-linked peptide

<400> SEQUENCE: 19

Arg Gln Ile Lys Ile Trp Phe Gln Asn Arg Arg Met Lys Trp Lys Lys
1               5                   10                  15

Ala Ala Ala Val Leu Ser Ala
            20

<210> SEQ ID NO 20
<211> LENGTH: 15
<212> TYPE: DNA
<213> ORGANISM: Artificial
<220> FEATURE:
<223> OTHER INFORMATION: synthetic oligonucleotide

<400> SEQUENCE: 20
agtttggcgc gaaat                                                    15

<210> SEQ ID NO 21
<211> LENGTH: 5
<212> TYPE: PRT
<213> ORGANISM: Artificial
<220> FEATURE:
<223> OTHER INFORMATION: conserved motif in E2F-1 and DP1
<220> FEATURE:
<221> NAME/KEY: misc_feature
<222> LOCATION: (3)..(3)
<223> OTHER INFORMATION: Xaa is Ile or Val or conservative substitutions
      or Ile or Val

<400> SEQUENCE: 21

Arg Arg Xaa Tyr Asp
1               5

<210> SEQ ID NO 22
<211> LENGTH: 4
<212> TYPE: PRT
<213> ORGANISM: Artificial
<220> FEATURE:
<223> OTHER INFORMATION: Spacer peptide

<400> SEQUENCE: 22

Gly Gly Gly Ser
1

<210> SEQ ID NO 23
<211> LENGTH: 24
<212> TYPE: DNA
<213> ORGANISM: Artificial
<220> FEATURE:
<223> OTHER INFORMATION: E2F-1 forward primer

<400> SEQUENCE: 23
aggctggacc tggaaactga ccat                                          24

<210> SEQ ID NO 24
<211> LENGTH: 25
<212> TYPE: DNA
<213> ORGANISM: Artificial
<220> FEATURE:
<223> OTHER INFORMATION: E2F-1 reverse primer
```

```
<400> SEQUENCE: 24
agctgcgtag tacagatatt catca                                       25

<210> SEQ ID NO 25
<211> LENGTH: 24
<212> TYPE: DNA
<213> ORGANISM: Artificial
<220> FEATURE:
<223> OTHER INFORMATION: TK forward primer

<400> SEQUENCE: 25
gcattaacct gcccactgtg ctgc                                        24

<210> SEQ ID NO 26
<211> LENGTH: 23
<212> TYPE: DNA
<213> ORGANISM: Artificial
<220> FEATURE:
<223> OTHER INFORMATION: TK reverse primer

<400> SEQUENCE: 26
gtgccgagcc tcttggtata ggc                                         23

<210> SEQ ID NO 27
<211> LENGTH: 24
<212> TYPE: DNA
<213> ORGANISM: Artificial
<220> FEATURE:
<223> OTHER INFORMATION: TS forward primer

<400> SEQUENCE: 27
gcgctacagc ctgagagatg aatt                                        24

<210> SEQ ID NO 28
<211> LENGTH: 24
<212> TYPE: DNA
<213> ORGANISM: Artificial
<220> FEATURE:
<223> OTHER INFORMATION: TS reverse primer

<400> SEQUENCE: 28
cttctgtcgt cagggttggt tttg                                        24

<210> SEQ ID NO 29
<211> LENGTH: 23
<212> TYPE: DNA
<213> ORGANISM: Artificial
<220> FEATURE:
<223> OTHER INFORMATION: RR-2 forward primer

<400> SEQUENCE: 29
tggaggatga gccgctgctg aga                                         23

<210> SEQ ID NO 30
<211> LENGTH: 25
<212> TYPE: DNA
<213> ORGANISM: Artificial
<220> FEATURE:
<223> OTHER INFORMATION: RR-2 reverse primer

<400> SEQUENCE: 30
ttgacacaag gcatcgtttc aatgg                                       25
```

```
<210> SEQ ID NO 31
<211> LENGTH: 24
<212> TYPE: DNA
<213> ORGANISM: Artificial
<220> FEATURE:
<223> OTHER INFORMATION: synthetic forward primer

<400> SEQUENCE: 31
aggaaccgcc gccgttgttc ccgt                                              24

<210> SEQ ID NO 32
<211> LENGTH: 24
<212> TYPE: DNA
<213> ORGANISM: Artificial
<220> FEATURE:
<223> OTHER INFORMATION: synthetic reverse primer

<400> SEQUENCE: 32
ctgcctgcaa agtcccggcc actt                                              24

<210> SEQ ID NO 33
<211> LENGTH: 16
<212> TYPE: PRT
<213> ORGANISM: Artificial
<220> FEATURE:
<223> OTHER INFORMATION: penetratin

<400> SEQUENCE: 33

Arg Gln Ile Lys Ile Trp Phe Gln Asn Arg Arg Ile Lys Trp Lys Lys
 1               5                  10                  15

<210> SEQ ID NO 34
<211> LENGTH: 23
<212> TYPE: PRT
<213> ORGANISM: artificial
<220> FEATURE:
<223> OTHER INFORMATION: penetratin

<400> SEQUENCE: 34

Arg Gln Ile Lys Ile Trp Phe Gln Asn Arg Arg Ile Lys Trp Lys Lys
 1               5                  10                  15

His His His Arg Leu Ser His
                20
```